(12) United States Patent
Tsui et al.

(10) Patent No.: US 8,895,254 B2
(45) Date of Patent: Nov. 25, 2014

(54) BIOMARKERS FOR ANKYLOSING SPONDYLITIS

(75) Inventors: Florence Wing Ling Tsui, Oakville (CA); Robert Davies Inman, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/233,342

(22) PCT Filed: Jul. 12, 2012

(86) PCT No.: PCT/CA2012/000667
§ 371 (c)(1),
(2), (4) Date: Feb. 25, 2014

(87) PCT Pub. No.: WO2013/010254
PCT Pub. Date: Jan. 24, 2013

(65) Prior Publication Data
US 2014/0193844 A1    Jul. 10, 2014

Related U.S. Application Data

(60) Provisional application No. 61/509,186, filed on Jul. 19, 2011.

(51) Int. Cl.
*G01N 33/53* (2006.01)
*G01N 33/564* (2006.01)
*C07K 14/47* (2006.01)
*G01N 33/68* (2006.01)

(52) U.S. Cl.
CPC ........ *G01N 33/564* (2013.01); *G01N 2800/102* (2013.01); *G01N 2800/56* (2013.01); *C07K 14/4713* (2013.01); *G01N 2800/10* (2013.01); *G01N 33/6893* (2013.01)
USPC ............................................. 435/7.1; 435/7.2

(58) Field of Classification Search
None
See application file for complete search history.

(56) References Cited

U.S. PATENT DOCUMENTS 7,285,532 B2 * 10/2007 Economides et al. ......... 514/8.8
7,578,999 B2 * 8/2009 Winkler et al. ............ 424/130.1

OTHER PUBLICATIONS

Appel H, Ruiz-Heiland G, Listing J et al. Altered skeletal expression of sclerostin and its link to radiographic progression in ankylosing spondylitis. Arthritis Rheum 2009;60:3257-62.
Chandra, et al., "Novel multiplex technology for diagnostic characterization of rheumatoid arthritis." Arthritis Res Ther. 13(3):R102, 2011.
Genbank Database NCBI Accession No. AAA83259 "noggin [*Homo sapiens*]" Dec. 13, 1995.
Genbank Database NCBI Accession No. AAK16158 "SOST [*Homo sapiens*]" Mar. 6, 2001.
International Preliminary Report on Patentability in International Application No. PCT/CA2012/000667 mailed Jan. 21, 2014.
Lories RJ, Derese I, Luyten FP. Modulation of bone morphogenetic protein signalling inhibits the onset and progression of ankylosing enthesitis. J Clin Invest 2005;115:1571-9.
Maksymowych WP, Elewaut D, Schett G. Motion for debate: the development of ankylosis in ankylosing spondylitis is largely dependent on inflammation. Arthritis Rheum 2012;64:1713-9.
Rudwaleit M, van der Heijde D, Khan MA et al. How to diagnosis axial spondyloarthritis early. Ann Rheum Dis 2004;63:535-43.
Search Report and Written Opinion in International Application No. PCT/CA2012/000667 mailed Oct. 26, 2012.
Urshansky N, Mausner-Fainberg K, Auriel E et al. Reduced production of noggin by immune cells of patients with relapsing-remitting multiple sclerosis. J Neuroimmunol 2011;232:171-8.
van der Heijde D, Landewé R, Einstein S et al. Radiographic progression of ankylosing spondylitis after up to two years of treatment with etanercept. Arthritis Rheum 2008;58:1324-31.
Winkler, et al., "Noggin and Sclerostin Bone Morphogenetic Protein Antagonists Form a Mutually Inhibitory Complex." J Biol Chem. 279(35):36293-8, 2004.
Wright, et al., "Detection of Multiple Autoantibodies in Patients with Ankylosing Spondylitis Using Nucleic Acid Programmable Protein Arrays." Mol Cell Proteomics. 11(2):M9.00384, 2010.
Zambrano-Zaragoza JF, Duran-Avelar MJ, Rodriguez-Ocampo AN et al. The 30-Kd band from *Salmonella typhimurium*: IgM, IgA and IgG antibody response in patients with ankylosing spondylitis. Rheumatol. 2009;48:748-54.

* cited by examiner

*Primary Examiner* — Jacob Cheu
(74) *Attorney, Agent, or Firm* — Fulbright & Jaworski LLP

(57) ABSTRACT

There is described herein methods and peptides for detecting autoantibodies to NOG and/or SOST in a patient sample in order to diagnose of prognosticate Ankylosing Spondylitis in the patient.

15 Claims, 20 Drawing Sheets

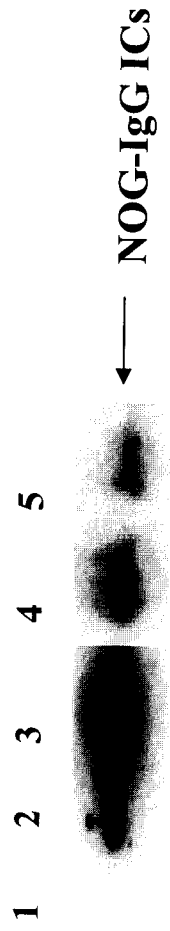

**NOG-IgG complexes are present in *NOG-ank* & *VECTOR-ank* sera**

→ NOG-IgG ICs

Lane 1: wild-type (BV1)
2: *VECTOR-ank* (DE2)
3: *NOG-ank* (DE1)
4: *NOG-ank* (EO1)
5: *VECTOR-ank* (EO2)

- IgGs & NOG-IgG complexes (ICs) depleted from mouse sera using protein G beads
- Eluates from protein G beads run on SDS-PAGE
- Western blot probed with anti-mouse NOG
- Probed with HRP-protein G and developed using Supersignal West Femto substrate

Fig.1

NOG-IgG immune complexes (ICs) detected in serum from AS patient (lane 2)

- IgGs & NOG-IgG ICs depleted by protein G beads
- Denatured eluates run on SDS-PAGE, and transferred to Immobilon-P
- Western blot probed with anti-NOG NOG-IgG ICs

Fig.5a

Free antigens (NOG) detected in Igs-depleted sera

- Sera after protein G and protein A beads depletions
- Supernatants denatured, run on SDS-PAGE and transferred to Immobilon-P
- Western blot probed with anti-NOG free NOG

Fig.5b

Lane 1: normal serum
2: AS serum

Western blot of IPs (rHis-NOG) probed with HRP-Nickel
Lane 1: serum was used for immunoprecipitation (IP)
Lane 2: purified IgG from the same serum (depleted of antigens) was used for IP

Fig.7a   Note: IP of the recombinant His-NOG using human serum (lane 1) showed low signals.

Free antigens (NOG) are recovered from the acidic eluate of IgG immune complexes (ICs)

Western blot of separated antigens from IgG ICs probed with anti-NOG (top panel)

Fig.7b

Likely initiating epitopes on NOG

Autoantigen complementarity:

```
                                          77
NOG         QHYLHIRPAPSDNLPLVDLIEHPDPIFDPKEKDLNETLLRSLLGGHYDPGFMATSPPEDRPGGGGAAGGA
NOG c-peptide LVIEVHARCGAVVQGQHVEDFVWVRDKVGLFLIQVLRQQARQEPAVVWAEHGGRGLVPGAPAPTCSPAR
``` underlined amino acids: homology with *Salmonella, Shigella, Klebsiella, Enterobacteria & E. coli* (XGPRT)

```
                                          54
NOG         QHYLHIRPAPSDNLPLVDLIEHPDPIFDPKEKDLNETLLRSLLGGHYDPGFMATSPPEDRPGGGGAAGGA
NOG c-peptide                                   KVGLFLIQVLRQQARQEP
``` underlined amino acids: homology with *Salmonella enterica* (regulatory protein)

Fig.8

NOG dimer

BMP7 dimer

Epitope N77
Epitope N54

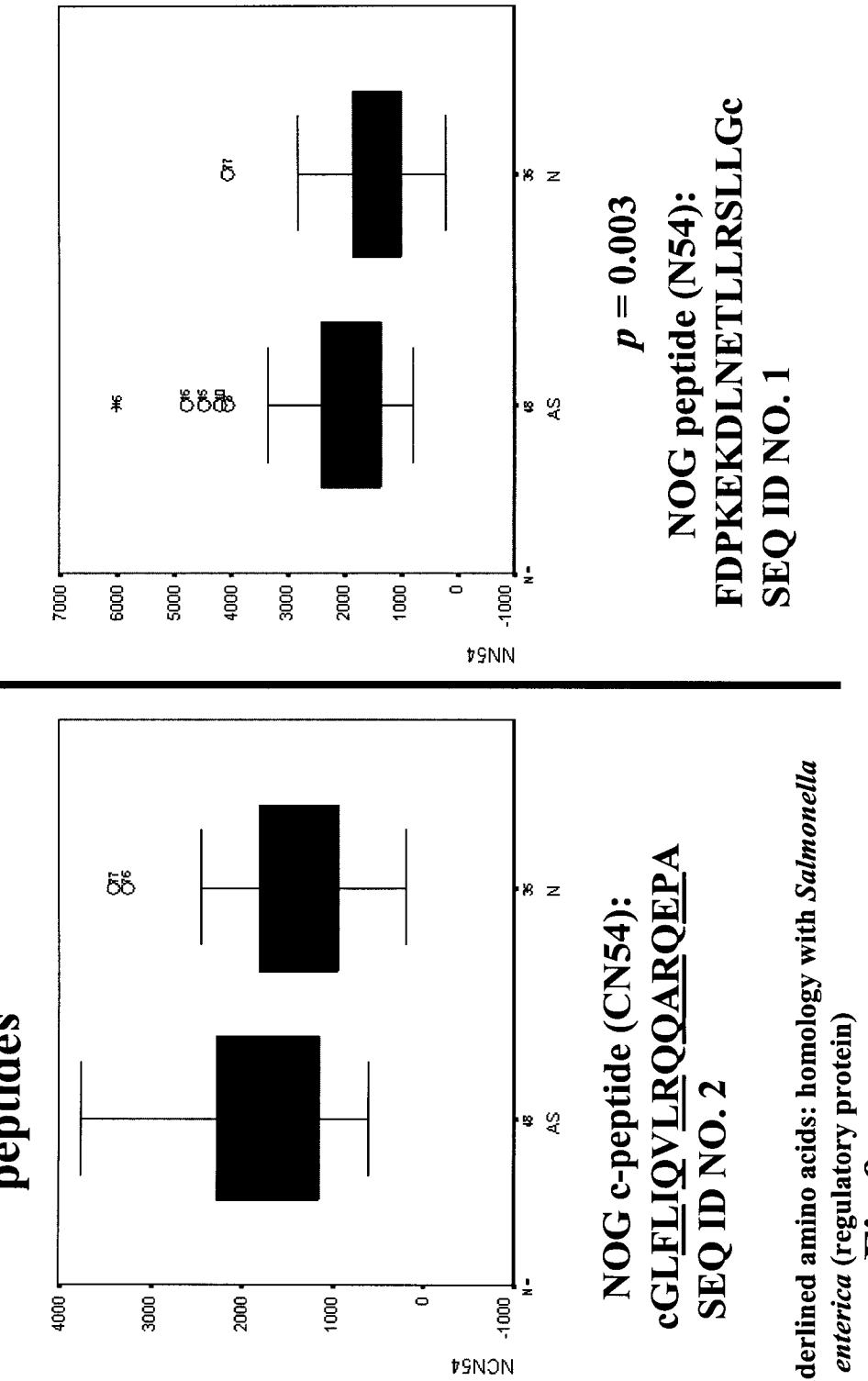

Autoantigen complementarity:

N-glycosylation signals
↓↓

```
                                                   54
NOG             QHYLHIRPAPSDNLPLVDLIEHPDPIFDPKEKDLNETLLRSLLGGHYDPGFMATSPPEDRPG
NOG c-peptide                                      KVGLFLIQVLRQQARQEP
``` underlined amino acids: homology with *Salmonella enterica* (regulatory protein)

Molecular mimicry:

```
                                          148
SOST                                    TRFHNQSE---LKDFG
Bacterial glycosyl transferase            FHNQSdygvLKDF
  (Haliscomenobacter hydrossis)
```

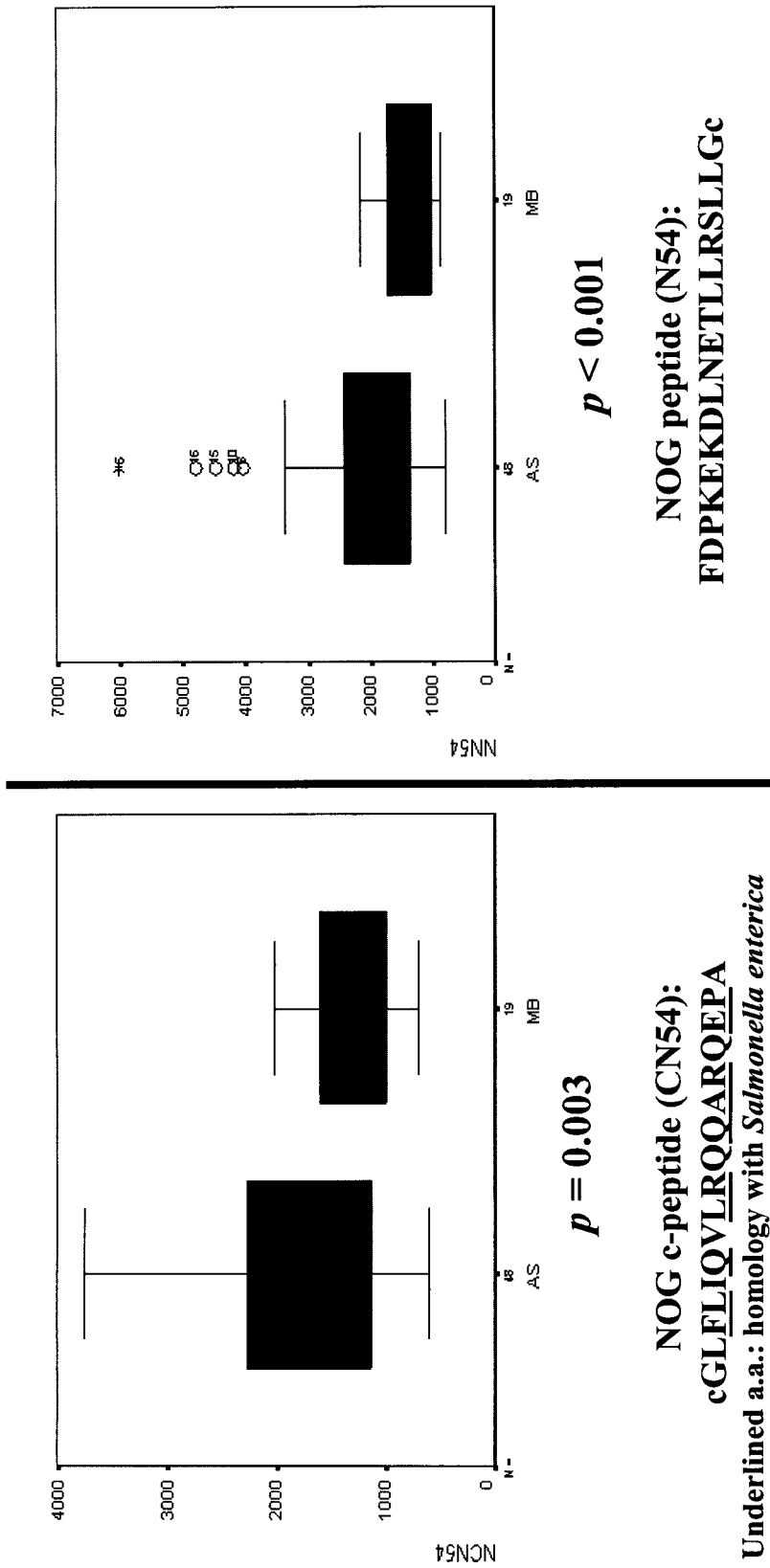
Fig.13a  AS: ankylosing spondylitis; MB: mechanical back-pain

NOG/SOST-IgG complexes are present in *NOG-ank* & *VECTOR-ank* sera

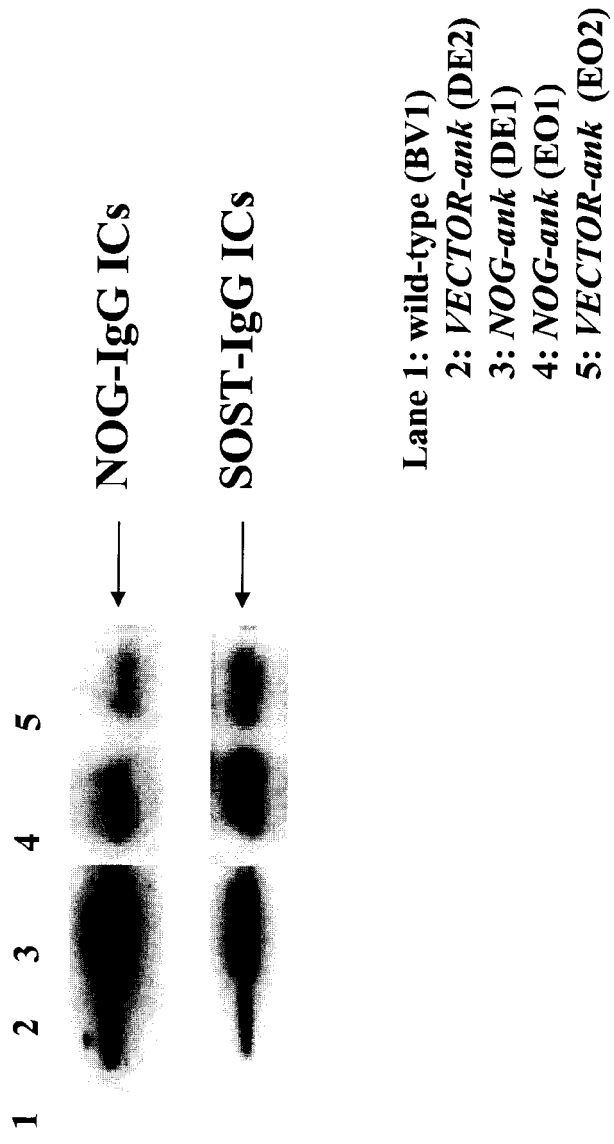

Lane 1: wild-type (BV1)
2: *VECTOR-ank* (DE2)
3: *NOG-ank* (DE1)
4: *NOG-ank* (EO1)
5: *VECTOR-ank* (EO2)

Fig. 15

- IgGs & NOG/SOST-IgG complexes (ICs) depleted from mouse sera using protein G beads
- Eluates from protein G beads divided into 2 aliquots, run on SDS-PAGE
- one western blot probed with anti-mouse NOG and the other probed with anti-mouse SOST
- Both blots probed with HRP-protein G and developed using Supersignal West Femto substrate

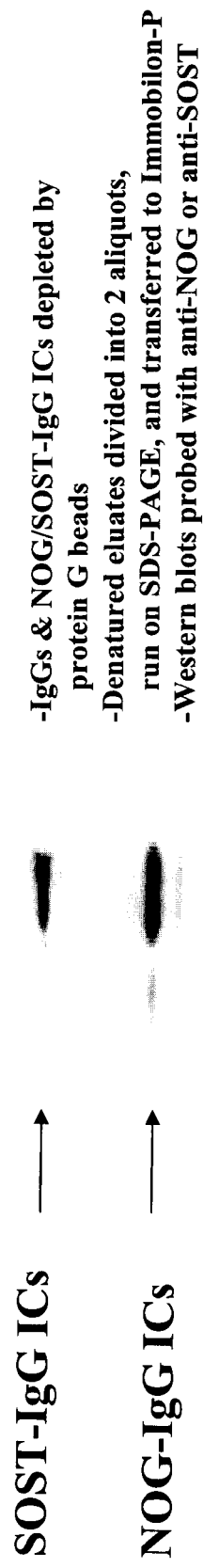
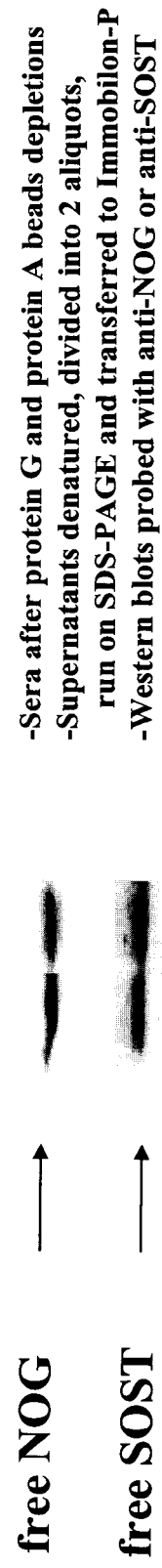

Fig.18a NOG/SOST-IgG immune complexes (ICs) are present in sera from AS patients SOST ICs
- IgGs & NOG/SOST-IgG ICs depleted by protein G beads
- Denatured eluates divided into 2 aliquots, run on SDS-PAGE, and transferred to Immobilon-P
- Western blots probed with anti-NOG or anti-SOST NOG-IgG ICs

Fig.18b Free antigens (NOG/SOST) are detected in Igs-depleted sera free NOG
- Sera after protein G and protein A beads depletions
- Supernatants denatured, divided into 2 aliquots, run on SDS-PAGE and transferred to Immobilon-P
- Western blots probed with anti-NOG or anti-SOST free SOST Lane 1: normal serum
2: AS serum

SEQUENCE LISTING

```
<160> NUMBER OF SEQ ID NOS: 5

<210> SEQ ID NO 1
<211> LENGTH: 18
<212> TYPE: PRT
<213> ORGANISM: Homo sapiens

<400> SEQUENCE: 1

Phe Asp Pro Lys Glu Lys Asp Leu Asn Glu Thr Leu Leu Arg Ser Leu
1               5                   10                  15

Leu Gly

<210> SEQ ID NO 2
<211> LENGTH: 17
<212> TYPE: PRT
<213> ORGANISM: Homo sapiens

<400> SEQUENCE: 2
```

```
Gly Leu Phe Leu Ile Gln Val Leu Arg Gln Gln Ala Arg Gln Glu Pro
1               5                   10                  15
Ala

<210> SEQ ID NO 3
<211> LENGTH: 13
<212> TYPE: PRT
<213> ORGANISM: Homo sapiens

<400> SEQUENCE: 3

Gly Phe Met Ala Thr Ser Pro Pro Glu Asp Arg Pro Gly
1               5                   10

<210> SEQ ID NO 4
<211> LENGTH: 14
<212> TYPE: PRT
<213> ORGANISM: Homo sapiens

<400> SEQUENCE: 4

Trp Ala Glu His Gly Gly Arg Gly Gly Leu Val Pro Gly Ala
1               5                   10

<210> SEQ ID NO 5
<211> LENGTH: 13
<212> TYPE: PRT
<213> ORGANISM: Homo sapiens

<400> SEQUENCE: 5

Thr Arg Phe His Asn Gln Ser Glu Leu Lys Asp Phe Gly
1               5                   10
```

BIOMARKERS FOR ANKYLOSING SPONDYLITIS

RELATED APPLICATIONS

This application is a national phase application under 35 U.S.C. §371 of International Application No. PCT/CA2012/000667 filed Jul. 12, 2012, which claims priority to U.S. Provisional Application No. 61/509,186 filed Jul. 19, 2011. The entire contents of each of the above-referenced disclosures is specifically incorporated herein by reference without disclaimer.

FIELD OF THE INVENTION

The invention relates to Ankylosing Spondylitis and more particularly to biomarkers therefor.

BACKGROUND OF THE INVENTION

Ankylosing spondylitis (AS), with a prevalence of 0.15-1.8%[1], is an under-recognized chronic disease which affects predominantly young men. A recent estimate of the US population concluded that there are approximately 2 million people with axial Spondylarthritis (SpA)[2]. The diagnosis of AS is made from a combination of clinical features[1], and the presence of radiographic evidence of sacroiliitis which may be detected only after many years of inflammatory back pain. It is not uncommon for a delay of 5-10 years after the initial onset of symptoms before the diagnosis is made[3,4]. The availability of biomarkers would not only facilitate rapid diagnosis, but would also provide better assessment, prognosis and management of the disease.

The hallmark of AS is neo-ossification at the site of joint inflammation. Biologics involving TNF-α blockage are very effective for controlling joint inflammation. However, they have no major impact on structural damage and ankylosis progression in AS[5]. Novel agents targeting ankylosis are required to fundamentally alter the natural history of this debilitating disease.

Results from genetic studies, animal models and therapy involving TNF blockers suggest that the gut-joint axis plays a critical role in the pathogenesis of SpA[6]. For decades, a relationship between reactive arthritis (ReA) and certain enterobacteria (e.g. *Salmonella, Yersinia, Shigella* and *Klebsiella*) has been noted[7]. Some ReA patients eventually develop AS. The evidence for the association between AS and bacterial infections is controversial[8,9].

There is an ongoing debate regarding whether inflammation and ankylosis in AS are linked events or independent processes[10,11]. Research on AS in humans subjects is limited by restricted access to target tissues, but animal studies can shed light on mechanisms involved in the joint ankylosing process. ank/ank (progressive ankylosis) mice represent an informative model for the study of joint ankylosis in AS due to similarities in the pattern of ankylosis (peripheral and axial) and aberrant Wnt-β-catenin signaling[12,13]. AS has long been viewed as a seronegative disease, notable for the absence of autoantibodies (autoabs). More recently, a reported protein microarray screening of patient plasma revealed multiple AS-specific IgG-autoabs directed against skeletal/connective tissue antigens[14].

SUMMARY OF THE INVENTION

In an aspect, there is provided a method for diagnosing a subject with Ankylosing Spondylitis comprising providing a sample from the subject; detecting a level of autoantibodies to at least one of (Noggin) NOG and (Sclerostin) SOST in the sample; comparing the level of autoantibodies detected in b. to a level of autoantibodies in a control sample; wherein a relatively higher level of autoantibodies in the subject sample compared to the control sample is indicative of Ankylosing Spondylitis in the subject.

In an aspect, there is provided a method for prognosticating Ankylosing Spondylitis in a subject comprising: providing a sample from the subject; detecting a level of autoantibodies to at least one of NOG and SOST in the sample; comparing the level of autoantibodies detected in b. to a level of autoantibodies in a control sample; wherein a relatively higher level of autoantibodies in the subject sample compared to the control sample is at least one of (i) indicative of the likelihood of the subject to have progression in ankylosis and (ii) a predictor of severity of disease.

In an aspect, there is provided an isolated peptide comprising conserved residues, the conserved residues being one of: residues 5-18 of N54 (SEQ ID NO. 1) or conservative amino acid substitutions thereof; residues 3, 4, 6, 8, 9, 11, 12, 13, 15 and 16 of CN54 (SEQ ID NO. 2), preferably residues 3-16, or conservative amino acid substitutions thereof; residues 6-13 of N77 (SEQ ID NO. 3 or conservative amino acid substitutions thereof); residues 7-14 CN76 (SEQ ID NO. 4) or conservative amino acid substitutions thereof; and residues 3-7 and 9-12 of S146 (SEQ ID NO. 5), preferably residues 3-12, or conservative amino acid substitutions thereof.

In an aspect, there is provided an assay for diagnosing a subject with Ankylosing Spondylitis comprising:
  a. providing a sample from the subject;
  b. detecting a level of autoantibodies to at least one of NOG and SOST in the sample;
  c. comparing the level of autoantibodies detected in b. to a level of autoantibodies in a control sample;
  wherein a relatively higher level of autoantibodies in the subject sample compared to the control sample is indicative of Ankylosing Spondylitis in the subject.

In an aspect, there is provided an assay for prognosticating Ankylosing Spondylitis in a subject comprising:
  a. providing a sample from the subject;
  b. detecting a level of autoantibodies to at least one of NOG and SOST in the sample;
  c. comparing the level of autoantibodies detected in b. to a level of autoantibodies in a control sample;
  wherein a relatively higher level of autoantibodies in the subject sample compared to the control sample is at least one of (i) indicative of the likelihood of the subject to have progression in ankylosis and (ii) a predictor of severity of disease.

In an aspect, there is provided a kit for diagnosing a subject with Ankylosing Spondylitis or prognosticating Ankylosing Spondylitis in a subject comprising at least one peptide capable of binding to autoantibodies to at least one of NOG and SOST.

BRIEF DESCRIPTION OF FIGURES

These and other features of the preferred embodiments of the invention will become more apparent in the following detailed description in which reference is made to the appended drawings wherein:

FIG. 1 shows NOG-IgG complexes are present in NOG-ank & VECTOR-ank sera. IgGs & NOG-IgG complexes (ICs) were depleted from mouse sera using protein G beads and eluates from protein G beads run on SDS-PAGE. Western blot was probed with anti-mouse NOG. Probed with HRP-protein G and developed using Supersignal West Femto substrate.

FIG. 5a shows NOG-IgG immune complexes (ICs) detected in serum from AS patient (lane 2). IgGs & NOG-IgG ICs were depleted by protein G beads. Denatured eluates were run on SDS-PAGE and transferred to Immobilon-P. Western blot was probed with anti-NOG.

FIG. 5b shows free antigens (NOG) detected in IgG-depleted sera. Sera recovered after protein G and protein A beads depletions. Supernatants were denatured, run on SDS-PAGE and transferred to Immobilon-P. Western blot was probed with anti-NOG.

FIG. 7a shows Western blot of IPs (rHis-NOG) probed with HRP-Nickel.

FIG. 7b shows Western blot of separated antigens from IgG ICs probed with anti-NOG (top panel).

FIG. 8 shows likely initiating epitopes on NOG.

FIGS. 9a and 9b are ELISAs showing binding of antigen-free IgGs to four peptides.

FIG. 10 shows homology of NOG and SOST peptides with bacterial proteins.

FIGS. 13a and 13b are ELISAs showing binding of antigen-free IgGs to four peptides.

FIG. 15 shows NOG/SOST-IgG complexes are present in NOG-ank & VECTOR-ank sera. IgGs & NOG/SOST-IgG complexes (ICs) were depleted from mouse sera using protein G beads. Eluates from protein G beads were divided into 2 aliquots and run on SDS-PAGE. One Western blot was probed with anti-mouse NOG and the other probed with anti-mouse SOST. Both blots were probed with HRP-protein G and developed using Supersignal West Femto substrate.

FIG. 18a shows NOG/SOST-IgG immune complexes (ICs) are present in sera from AS patients. IgGs & NOG/SOST-IgG ICs were depleted by protein G beads. Denatured eluates were divided into 2 aliquots, run on SDS-PAGE, and transferred to Immobilon-P. Western blots were probed with anti-NOG or anti-SOST.

FIG. 18b shows Free antigens (NOG/SOST) are detected in Igs-depleted sera. Sera supernatants, after protein G and protein A beads depletions, were denatured, divided into 2 aliquots, run on SDS-PAGE and transferred to Immobilon-P. Western blots were probed with anti-NOG or anti-SOST.

DETAILED DESCRIPTION

Figure 2:
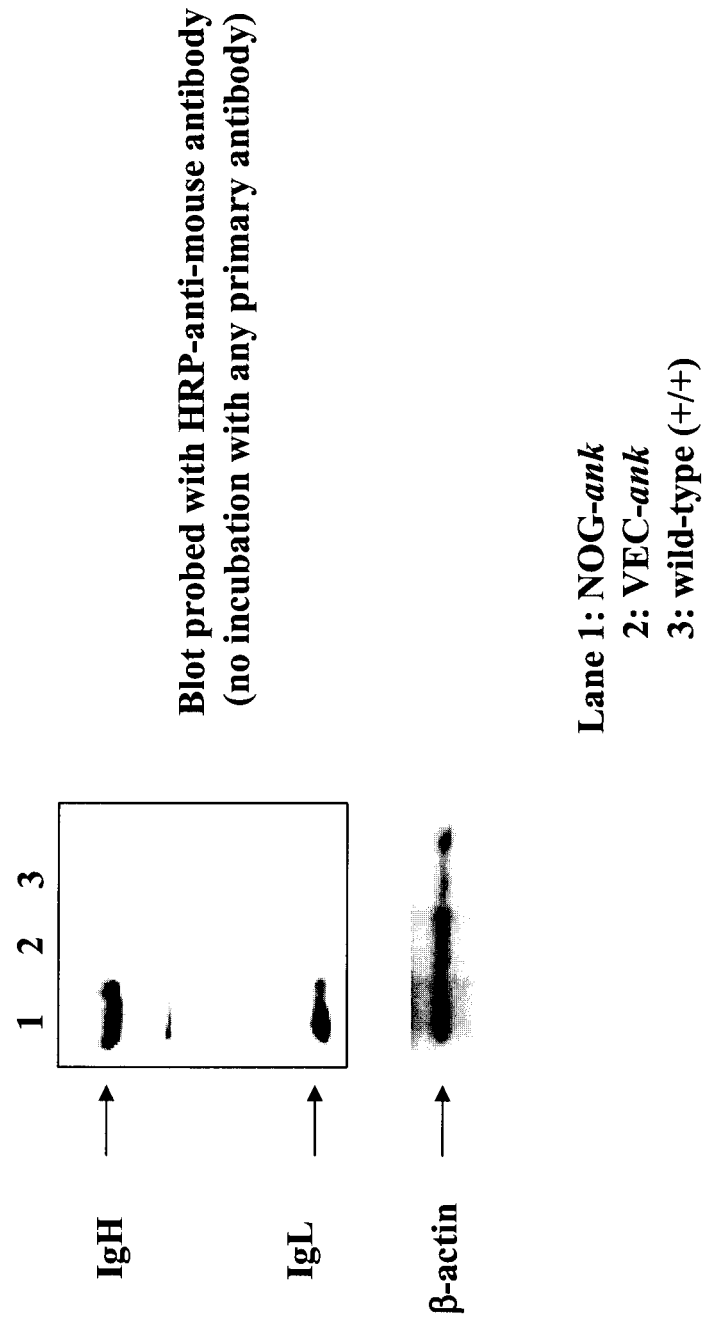
FIG. 2 shows presence of IgGs in paw lysates of NOG-ank mice. Blot was probed with HRP-anti-mouse antibody (no incubation with any primary antibody).

In the following description, numerous specific details are set forth to provide a thorough understanding of the invention. However, it is understood that the invention may be practiced without these specific details.

Ankylosing spondylitis (AS) has long been viewed as a seronegative disease; however, circumstantial evidence has implicated it as an autoimmune disease. We explored the generation and the pathophysiological role of autoantibodies (autoabs) and immune complexes (ICs) in ankylosis in AS patients.

IgG-ICs from human sera were detected by immunoprecipitation and Western blot analyses. Protein databases were searched for amino acid homologies between autoantigens (noggin [NOG] or sclerostin [SOST]) and/or their complementary-peptide (c-peptides) sequences in comparison with enterobacterial proteins. Potential initiating epitopes were identified using peptide-binding ELISAs.

Natural IgG autoabs to NOG and SOST are present in AS sera at higher levels than healthy controls. These autoabs exist mainly as ICs and their presence is masked in serum due to excess free antigens. Based on their structural/sequence homologies to arthritogenic enterobacterial proteins, critical epitopes on NOG and SOST were identified. Binding of AS IgGs to these epitopes was significantly higher than those from normal controls or individuals with mechanical back pain.

Arthritigenic enterobacterial antigens are candidate triggers of autoimmune responses to antagonists of signaling pathways involved in ossification, which could contribute to the progressive ankylosis in AS patients. Our results have two important implications which may aid the diagnosis and management of AS: 1. From a clinical perspective, peptide-binding ELISAs can be used to differentiate patients with inflammatory versus mechanical back pain and to define AS subsets; 2. From a conceptual perspective, autoimmunity to NOG/SOST may represent the missing link between inflammation and ankylosis in AS.

In an aspect, there is provided a method for diagnosing a subject with Ankylosing Spondylitis comprising providing a sample from the subject; detecting a level of autoantibodies to at least one of NOG and SOST in the sample; comparing the level of autoantibodies detected in b. to a level of autoantibodies in a control sample; wherein a relatively higher level of autoantibodies in the subject sample compared to the control sample is indicative of Ankylosing Spondylitis in the subject.

In an aspect, there is provided a method for prognosticating Ankylosing Spondylitis in a subject comprising: providing a sample from the subject; detecting a level of autoantibodies to at least one of NOG and SOST in the sample; comparing the level of autoantibodies detected in b. to a level of autoantibodies in a control sample; wherein a relatively higher level of autoantibodies in the subject sample compared to the control sample is at least one of (i) indicative of the likelihood of the subject to have progression in ankylosis and (ii) a predictor of severity of disease.

In some embodiments, the level of autoantibodies in the sample compared to the control sample is 2-10× higher.

In some embodiments, the samples are one of serum, plasma and synovial fluid samples.

In some embodiments, the autoantibodies are pre-complexed with antigen. Preferably, the autoantibody is in a NOG-IgG immune complex, SOST-IgG immune complex or NOG/SOST-IgG immune complex.

In some embodiments, the level of autoantibodies to at least one of NOG and SOST in the sample is detected using at least one peptide capable of selectively binding to autoantibodies to at least one of NOG and SOST and described herein.

In an aspect, there is provided an isolated peptide comprising conserved residues, the conserved residues being one of: residues 5-18 of N54 (SEQ ID NO. 1) or conservative amino acid substitutions thereof; residues 3, 4, 6, 8, 9, 11, 12, 13, 15 and 16 of CN54 (SEQ ID NO. 2), preferably residues 3-16, or conservative amino acid substitutions thereof; residues 6-13 of N77 (SEQ ID NO. 3 or conservative amino acid substitutions thereof); residues 7-14 CN76 (SEQ ID NO. 4) or conservative amino acid substitutions thereof; and residues 3-7 and 9-12 of S146 (SEQ ID NO. 5), preferably residues 3-12, or conservative amino acid substitutions thereof.

Preferably, the conserved residues are one of: residues 5-18 of N54 (SEQ ID NO. 1); residues 3, 4, 6, 8, 9, 11, 12, 13, 15 and 16 of CN54 (SEQ ID NO. 2), preferably residues 3-16; residues 6-13 of N77 (SEQ ID NO. 3); residues 7-14 CN76 (SEQ ID NO. 4); and residues 3-7 and 9-12 of S146 (SEQ ID NO. 5), preferably residues 3-12.

In some embodiments, the peptide is 6-30 amino acids in length.

In some embodiments, the peptide is one of N54, CN54, N77, CN77 and S146.

In an aspect, there is provided an assay for diagnosing a subject with Ankylosing Spondylitis comprising:
d. providing a sample from the subject;
e. detecting a level of autoantibodies to at least one of NOG and SOST in the sample;
f. comparing the level of autoantibodies detected in b. to a level of autoantibodies in a control sample;
wherein a relatively higher level of autoantibodies in the subject sample compared to the control sample is indicative of Ankylosing Spondylitis in the subject.

In an aspect, there is provided an assay for prognosticating Ankylosing Spondylitis in a subject comprising:
d. providing a sample from the subject;
e. detecting a level of autoantibodies to at least one of NOG and SOST in the sample;
f. comparing the level of autoantibodies detected in b. to a level of autoantibodies in a control sample;
wherein a relatively higher level of autoantibodies in the subject sample compared to the control sample is at least one of (i) indicative of the likelihood of the subject to have progression in ankylosis and (ii) a predictor of severity of disease.

In an aspect, there is provided a kit for diagnosing a subject with Ankylosing Spondylitis or prognosticating Ankylosing Spondylitis in a subject comprising at least one peptide capable of binding to autoantibodies to at least one of NOG and SOST.

In some embodiments, the peptide is a peptide described herein.

In some embodiments, the kit further comprises instructions for use corresponding to a methods described herein.

In some embodiments, the kit further comprises reagents for detecting autoantibodies of at least one of NOG and SOST bound to the peptide.

As used herein, "polypeptide" and "protein" are used interchangeably and mean proteins, protein fragments, modified proteins, amino acid sequences and synthetic amino acid sequences. The polypeptide can be glycosylated or not. "Peptides" as used herein refer to short polypeptides, preferably being 6-30 amino acids in length.

As used herein "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer., Principles of Protein Structure, Springer-Verlag). Examples of amino acid groups defined in this manner include:
(i) a charged group, consisting of Glu and Asp, Lys, Arg and His,
(ii) a positively-charged group, consisting of Lys, Arg and His,
(iii) a negatively-charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly-polar group, consisting of Met and Cys,
(viii) a small-residue group, consisting of Ser, Thr, Asp, Asn, Gly, Ala, Glu, Gln and Pro,
(ix) an aliphatic group consisting of Val, Leu, Ile, Met and Cys, and
(x) a small hydroxyl group consisting of Ser and Thr.

In addition to the groups presented above, each amino acid residue may form its own group, and the group formed by an individual amino acid may be referred to simply by the one and/or three letter abbreviation for that amino acid commonly used in the art.

As used herein "fragment" relating to a polypeptide or polynucleotide means a polypeptide or polynucleotide consisting of only a part of the intact polypeptide sequence and structure, or the nucleotide sequence and structure, of the reference gene. The polypeptide fragment can include a C-terminal deletion and/or N-terminal deletion of the native polypeptide, or can be derived from an internal portion of the molecule. Similarly, a polynucleotide fragment can include a 3' and/or a 5' deletion of the native polynucleotide, or can be derived from an internal portion of the molecule.

The term "level" as used herein refers to a measurable level of a biomarker, for example, the level of proteins or portions thereof corresponding to the biomarker. In preferable embodiments, the level of autoantibodies is measured, for example, autoantibodies to NOG and SOST. A person skilled in the art would understand that levels of other products could also be measured, for example, the level of messenger RNA transcript expressed or of a specific exon or other portion of a transcript, the number or presence of DNA polymorphisms of the biomarkers, the enzymatic or other activities of the biomarkers, and the level of specific metabolites.

In addition, a person skilled in the art will appreciate that a number of methods can be used to determine the amount of a protein product of the biomarker of the invention, including immunoassays such as Western blots, ELISA, and immunoprecipitation followed by SDS-PAGE and immunocytochemistry.

As used herein, the term "control" refers to a specific value or dataset that can be used to prognose or classify the value e.g. level of autoantibodies obtained from the test sample associated with an outcome class. A person skilled in the art will appreciate that the comparison between the level of the biomarkers in the test sample and the level of the biomarkers in the control will depend on the control used.

The term "sample" as used herein refers to any fluid, cell or tissue sample from a subject that can be assayed for biomarker expression products and/or a reference expression profile, e.g. genes differentially expressed in subjects.

Advantages of the present invention are further illustrated by the following examples. The examples and their particular details set forth herein are presented for illustration only and should not be construed as a limitation on the claims of the present invention.

EXAMPLES

Methods and Materials
ank/ank Mice and Injection of noggin (nog)
ank/ank mice were generated by crossbreeding heterozygous mice. Systemic gene transfer of a noggin expression construct (provided by Dr. F. Luyten[15]) was carried out in 5-wks old ank/ank mice. The mutant mice (at least 4 pairs from the same litter) were injected intramuscularly with 200 µg of either NOG cDNA (NOG-ank) or empty vector DNA (VEC-ank). Injections were repeated every 3 wks for 3-4 cycles. Sera were taken from the injected mice at the end of the experiment. All animal procedures were approved by the University Health Network Animal Experimentation Committee.

Study Subjects
The study cohort was recruited from the Toronto Western Spondylitis Clinic. All subjects provided written informed consent for use of their serum samples. The study was approved by the University Health Network Research Ethics Board.

Purification of IgGs from Sera
As the respective free autoantigens (NOG and sclerostin [SOST]) are detected in human sera, it is imperative to isolate IgG autoabs free of the bound antigens before further characterization. To ensure that there are no ICs in the IgG preparations, ultrafiltration (Ultracel 100K) of acid eluted IgGs (from protein-G agarose) were used to generate autoantigen-free IgGs.

Western Blot Analyses
Human serum samples (2 µl each) were incubated with 20 µl of protein G agarose (50%) for 1 hr with shaking at room temperature. After washings, eluates from the protein G beads were divided into 2 aliquots, denatured, separated by SDS-PAGE, and transferred to Immobilon-P membrane. One blot was probed with rabbit anti-human NOG antibody (Sigma) and the other probed with a mouse monoclonal antibody to human SOST (R & D). After washings, both blots were probed with HRP-protein G, developed using Supersignal West Femto substrate (Pierce) and imaged. Visualized band volume signals were quantified by imaging. We used a standard normal serum for each Western blot and the relative amounts of NOG/SOST IgG-ICs were estimated as fold-change higher or lower than the normal standard. A standard AS patient serum was also included in each Western blot as a positive control.

Peptide Binding ELISAs
Peptides were generated with a terminal cysteine residue to enable covalent coupling to maleimide activated plates (Pierce). Excess maleimide groups were inactivated by cysteine-HCl. Antigen-free protein G-purified IgG (1 µg/ml or less for higher titers) were incubated with the peptide-coated plates for 1 hr. After washings, the plates were incubated with horseradish peroxidase (HRP)-anti-human IgG secondary antibody (Jackson), followed by HRP chromogenic substrates (Pierce) and read on an ELISA plate reader at 450 nm. For normalization of results from different plates, a standard curve using serial dilutions of a standard AS patient IgG was included in each 96-well plate. Results were expressed as arbitrary units relative to the standard AS IgG present in the total amount of IgGs from 1 ml of each serum sample.

Results and Discussion
Sera of NOG-ank Mice had Higher Levels of NOG-IgG ICs
While assessing whether injection of NOG-cDNA resulted in higher levels of NOG in the ank/ank mice, we encountered an unanticipated result: NOG-ank mice had high serum levels of NOG-IgG ICs (FIG. 1), and a large amount of IgGs were found in paw lysates of NOG-ank mice (FIG. 2). In VEC-ank or untreated ank/ank mice, significantly lower levels of NOG-IgG ICs were detected. However, no IgGs were found in paw lysates of ank/ank mice suggesting that in addition to quantitative differences, there are likely qualitative differences in the NOG-IgG ICs from NOG-ank versus ank/ank sera.

Figure 3:
FIG. 3 shows NOG-IgG immune complexes (ICs) are present at higher levels in AS patient sera. IgGs & NOG-IgG ICs were depleted from human sera using protein G beads. Eluates from protein G beads were run on SDS-PAGE. Western blot was probed with anti-human NOG. Probed with HRP-protein G and developed using Supersignal West Femto substrate.
Figure 4:
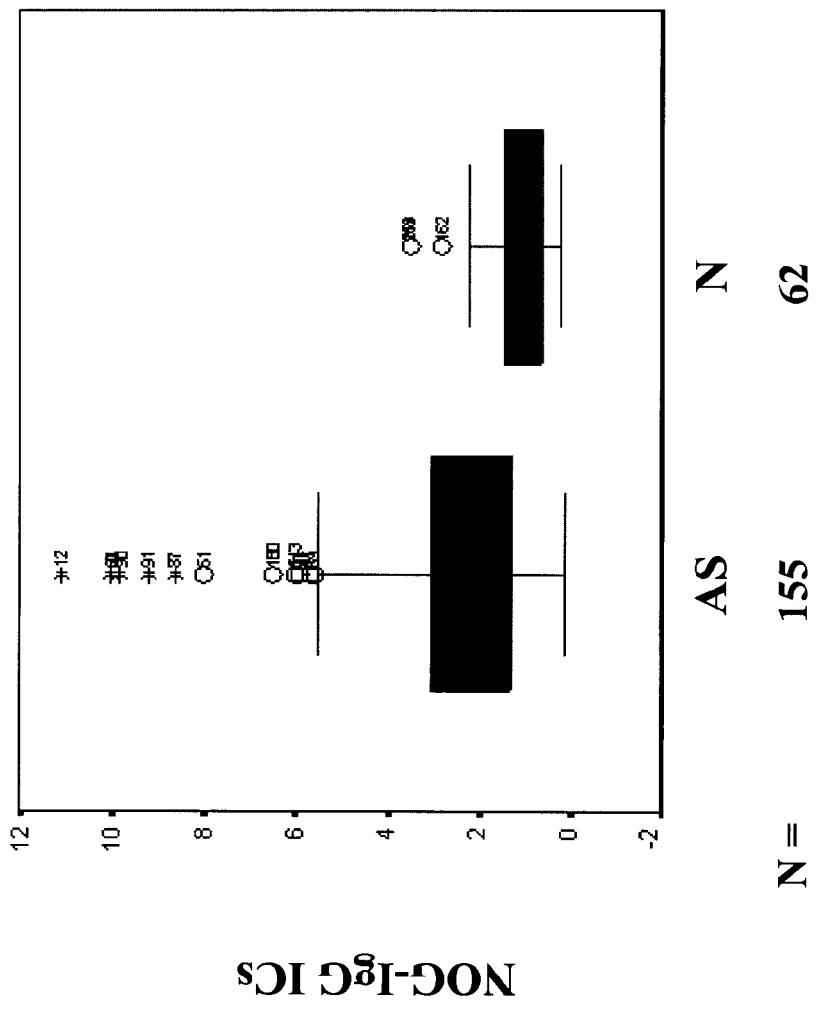
FIG. 4 shows higher levels of NOG-IgG ICs are present in sera from AS patients.
Figure 6:
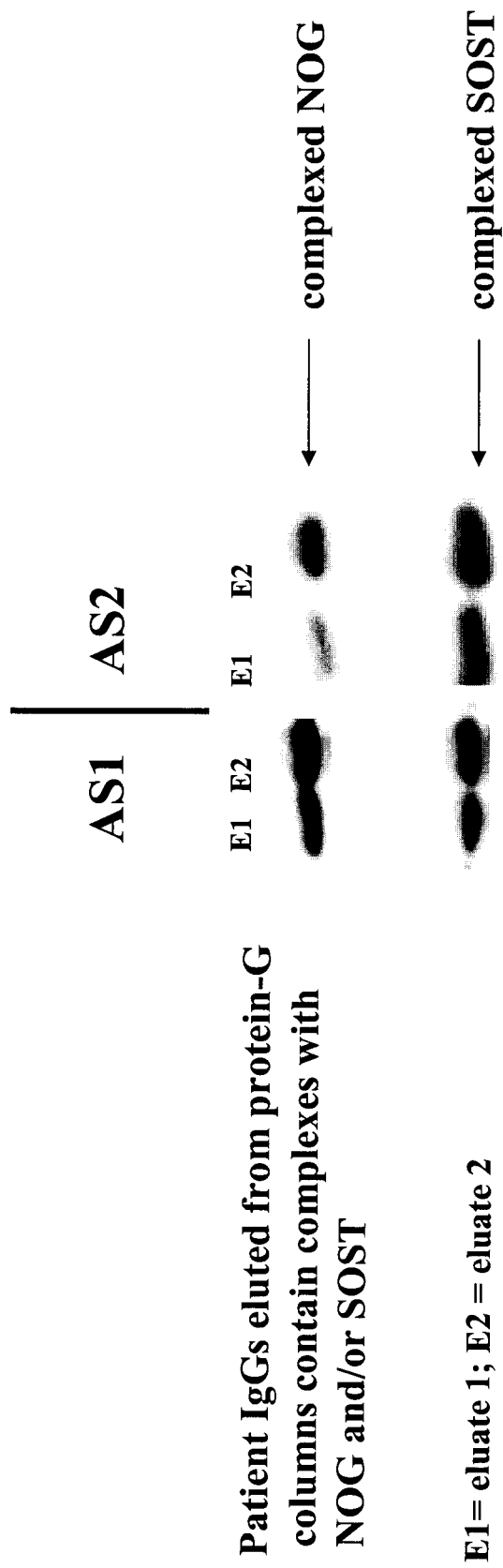
FIG. 6 shows patient IgGs eluted from protein-G columns contain complexes with NOG and/or SOST.

Identification of a Novel Natural Autoab to a BMP Antagonist (NOG) in Humans
In view of the novel finding of NOG-IgG ICs in ank/ank mice, we asked whether these IgG-ICs are present in human sera. Indeed, NOG-IgG ICs are present in normal human sera (n=62), but higher levels (up to 10-fold higher, i.e. between 2-10×) were detected in sera from AS patients (n=160; $p<0.001$; FIG. 3 and FIG. 4). AS has long been viewed as a seronegative disease by virtue of the absence of autoabs. NOG autoabs were not detected previously likely because both the antigen (NOG) and the antibodies exist as ICs in the sera and that the antigen is in excess; i.e. free NOG can be detected in Ig depleted sera (FIG. 5). A majority of NOG-IgG ICs were either not dissociated after acid elution from protein-G beads or they re-complexed when the eluted IgGs were neutralized (FIG. 6). To confirm the presence of NOG IgG ICs in human sera, we purified IgGs from patient sera using protein-G beads and acid elution. To remove bound NOG from the ICs, purified IgGs were subjected to ultrafiltration under acidic conditions (pH 2.7), using Amicon ultra filters (Ultracel 100K). The antigen-free ICs can bind to recombinant NOG protein with a His-tag (rHis-NOG; FIG. 7a) and were detected by probing with HRP-nickel. Free endogenous NOG released from the IgG-ICs can be detected by Western blots using an anti-NOG antibody (FIG. 7b).

Figure 9B:
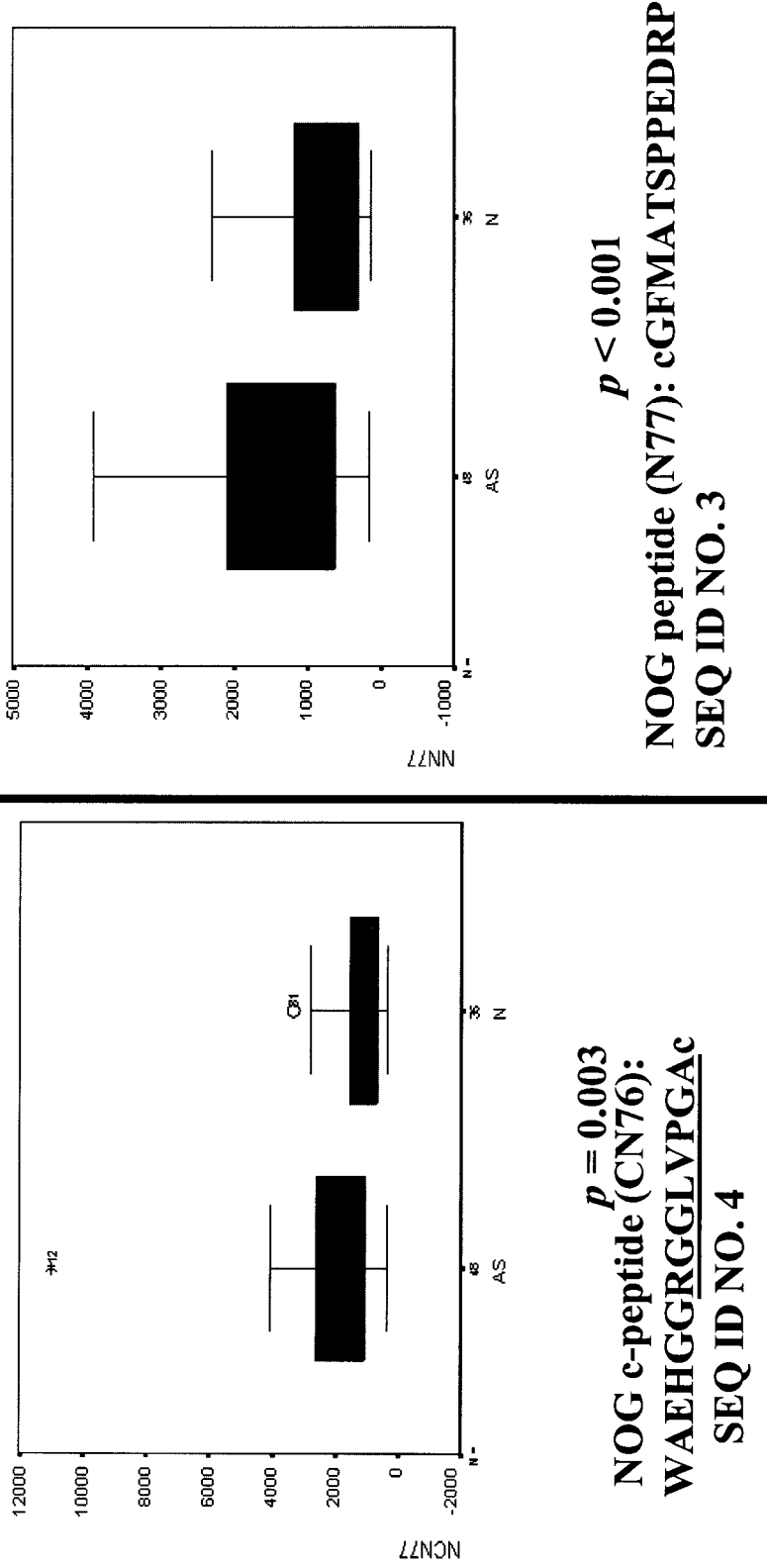

Enterobacterial Antigens Likely Trigger the Autoimmune Response to NOG in AS Patients
To assess whether molecular mimicry and/or autoantigen complementarity underlie the generation of NOG autoabs, we examined the NCBI databases for significant homologies. We found peptides complementary (c-peptides) to NOG bearing significant homologies to bacterial proteins (FIG. 8), and thus would have significant structural similarities. Based on the c-peptide homologies and antigenicity, we designed 2 pairs of peptides (NOG peptide N54 and its c-peptide CN54; NOG peptide N77 and its c-peptide CN77). NOG c-peptide CN54 has homology with a regulatory protein of *Salmonella enterica*, while NOG c-peptide CN77 shared an eight amino acid homology (RGGLVPG) with guanine-hypoxanthine phosphoribosyltransferase which is highly conserved in bacteria including *Salmonella, Shigella, Yersinia, Klebsiella* and *E. coli*. Compared to normal individuals (n=35), AS patients (n=48) had significantly higher levels of IgGs which bind to NOG peptide N54 (FIG. 9a; p=0.003), though there were no significant difference in the levels of IgGs which bind to NOG c-peptide CN54. For the NOG c-peptide CN77 and NOG peptide N77, AS patients have higher levels of IgGs binding of both peptides compared to those of the normal controls (FIG. 9b).

Figure 16:
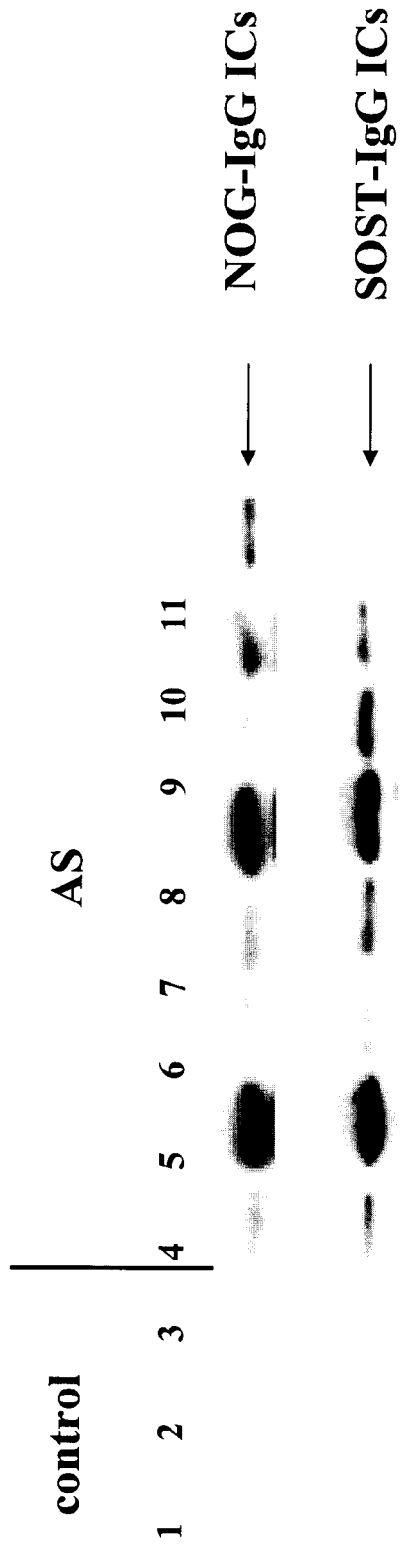
FIG. 16 shows NOG/SOST-IgG immune complexes (ICs) are present at higher levels in AS patient sera. IgGs & NOG/SOST-IgG complexes (ICs) were depleted from human sera using protein G beads. Eluates from protein G beads were divided into 2 aliquots and run on SDS-PAGE. One Western blot was probed with anti-human NOG and the other probed with anti-human SOST. Both blots were probed with HRP-protein G and developed using Supersignal West Femto substrate.
Figure 17:
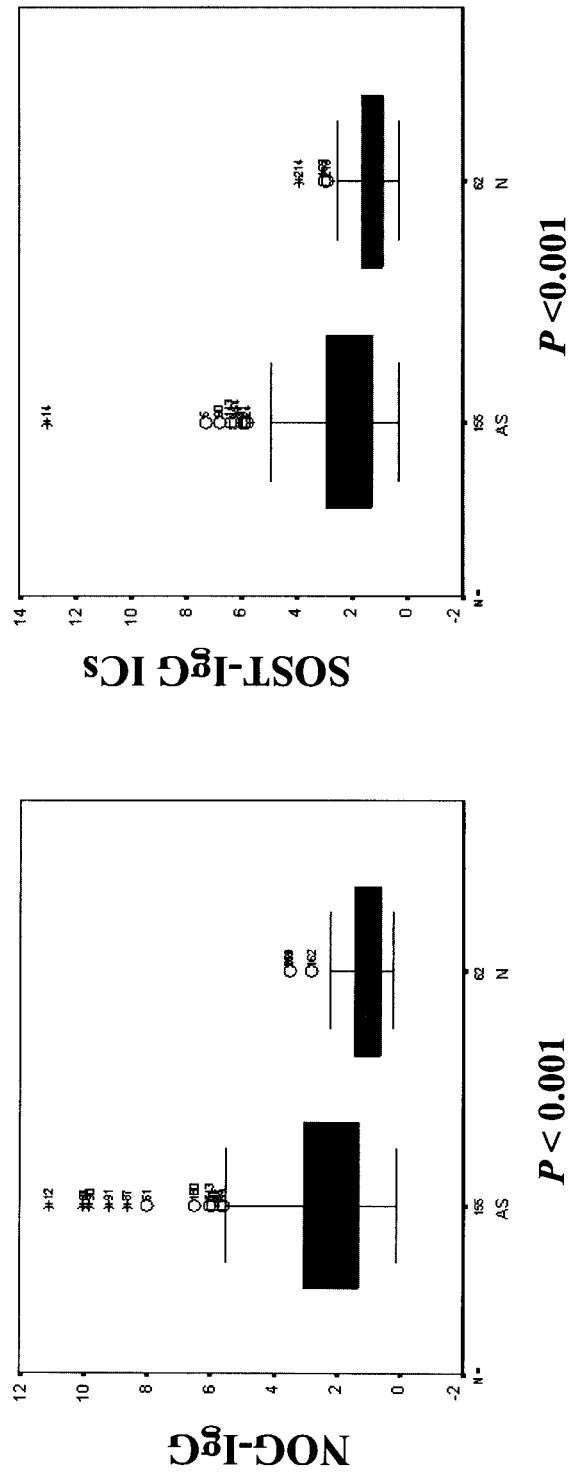
FIG. 17 shows higher levels of NOG/SOST-IgG ICs are present in sera from AS patients.

Sera from AS Patients have Higher Levels of Anti-SOST Autoantibodies Implicated by Molecular Mimicry It has been reported that NOG and SOST can form a mutually inhibitory complex[16]. We asked whether NOG autoantibodies recognize NOG-SOST complexes. Western blot analysis of protein G purified ank/ank IgGs, showed that presence of SOST and NOG-ank mice had higher levels of SOST complexed with IgGs (FIG. 15). Similarly, SOST proteins can be detected in protein G purified human IgGs and higher levels were detected in AS IgGs (FIG. 16). Next, we asked whether autoantibodies to SOST exist in human sera. Recombinant SOST proteins with a His-tag can be immunoprecipitated by human IgGs (FIG. 17) and higher levels of SOST IgG ICs were detected in AS sera than controls. Similar to human NOG-IgG ICs, we can recover free endogenous SOST proteins released from the IgG ICs via ultrafiltration under acidic conditions (FIG. 18).

Figure 11:
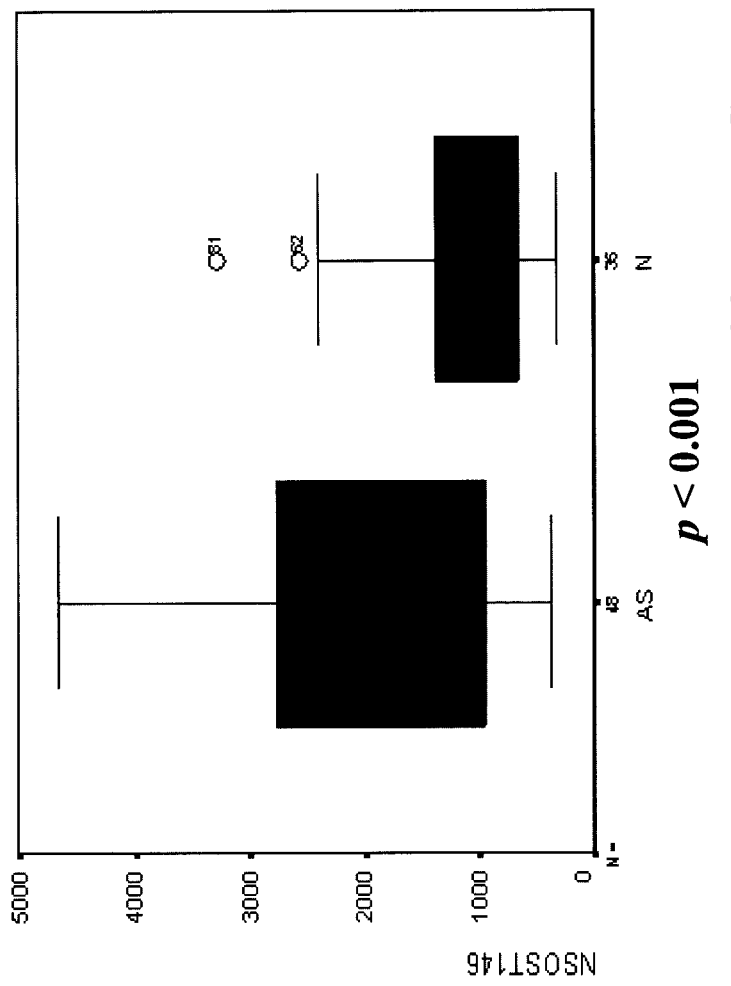
FIG. 11 shows is an ELISA showing binding of antigen-free IgGs to SOST peptide.
Figure 12:
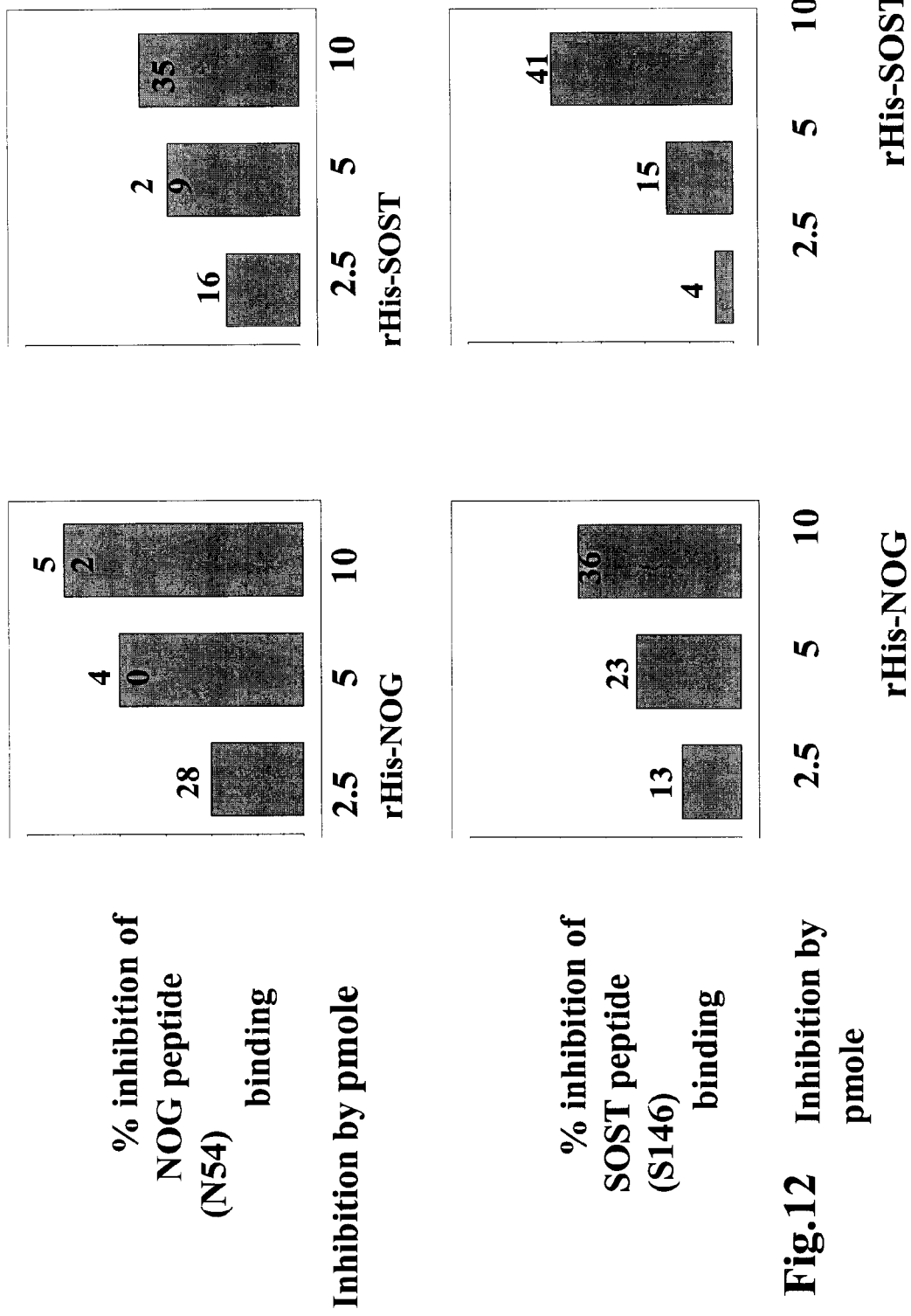
FIG. 12 shows binding of AS IgGs to NOG peptide (N54)/SOST peptide (S146) is inhibitable by rHis-NOG or rHis-SOST proteins.

The NOG peptide N54 contains N-glycosylation signals (N62 and T64). Protein database searches revealed a bacterial glycosyl transferase (*Hiliscomenobacter hydrossis*) bearing sequence homology with a Sclerostin (SOST) peptide (SOST S146; FIG. 10) located at the carboxyl-terminal end (after loop 3 of the SOST molecule). We asked whether this region represents one of the SOST epitopes and is recognized by human SOST autoabs. Results from peptide-binding ELISAs showed that AS patients have higher levels of IgGs recognizing this SOST peptide (S146) compared to normal controls (FIG. 11; p<0.001). Binding of AS IgGs to NOG peptide (N54) or SOST peptide (S146) was inhibited by rHis-NOG and rHis-SOST in a dose-dependent manner in both peptide binding assays (result of a representative experiment is shown in FIG. 12). No inhibition was observed using rHis-bcl$_2$ as a specificity control in both assays.

Figure 13B:
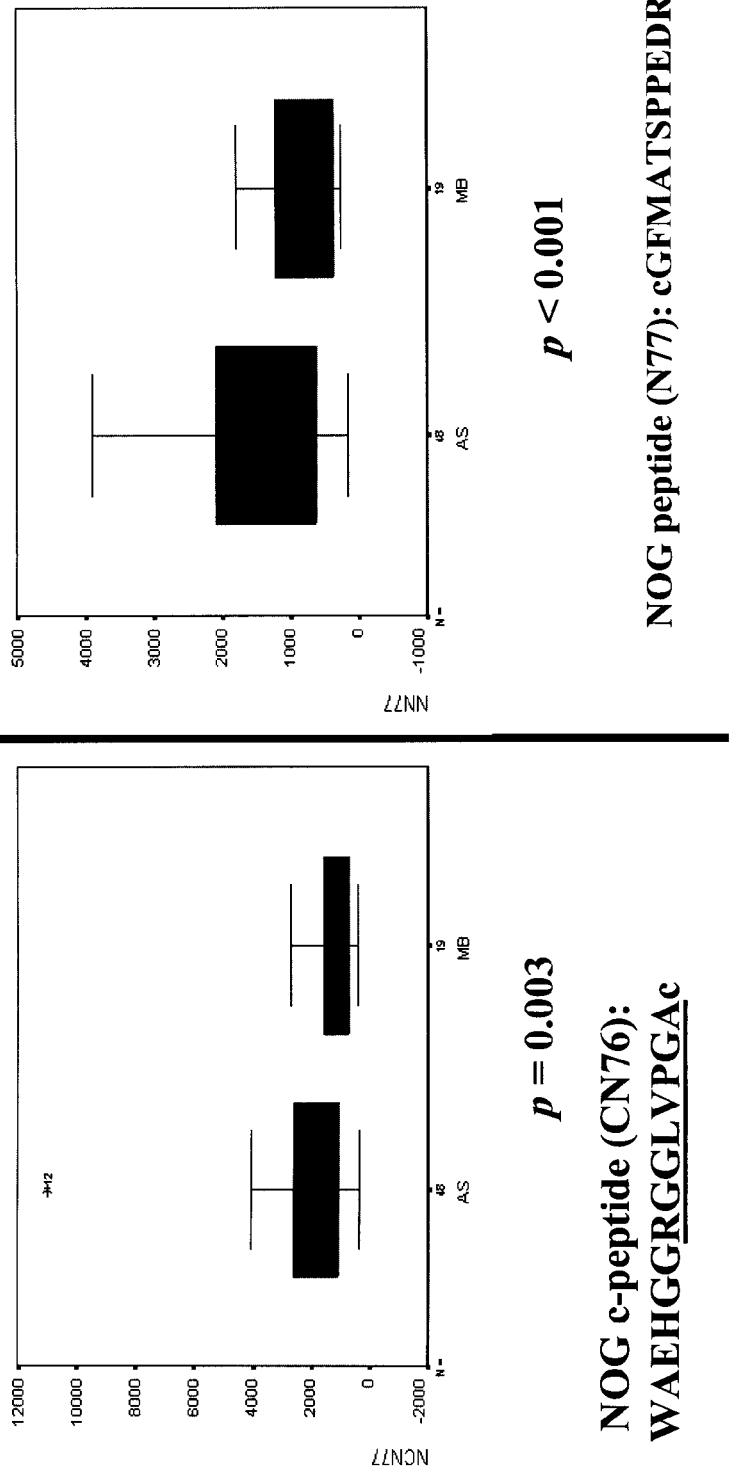
Figure 14:
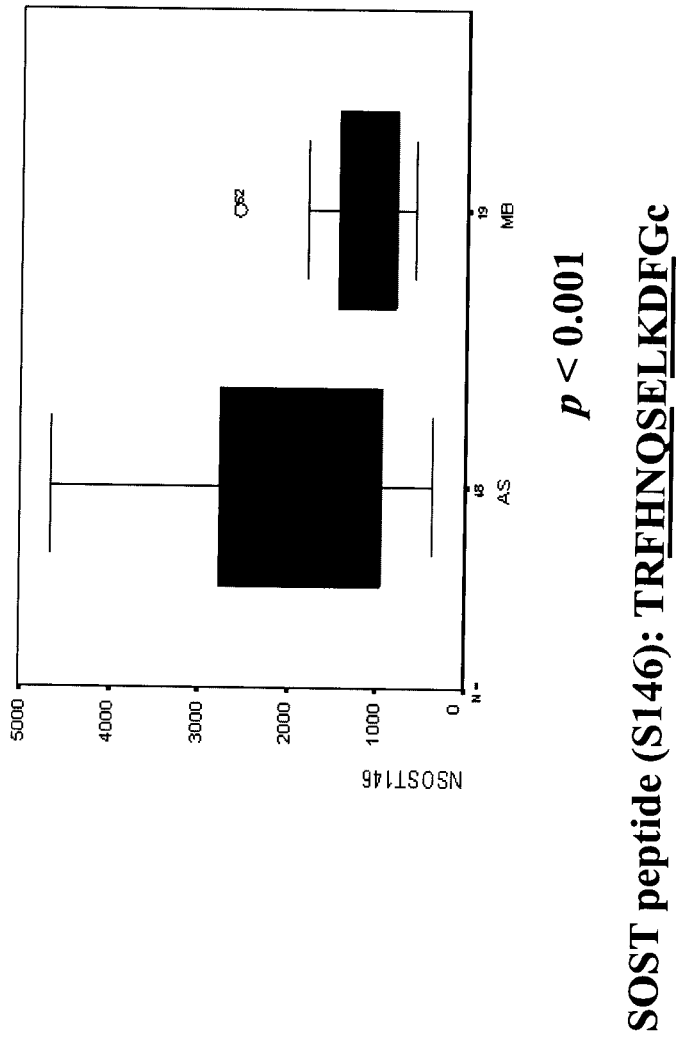
FIG. 14 is an ELISA showing binding of antigen-free IgGs to SOST peptide.

Autoantibodies to NOG/SOST Peptide Differentiate Patients with Inflammatory from Non-Inflammatory Back Pain We asked whether NOG/SOST peptide binding IgG levels can be used as a biomarker to improve diagnostic discrimination of whether a patient with chronic back pain has inflammatory back pain. We compared the IgG levels of AS versus individuals with mechanical back pain for binding to the 5 different peptides we previously used (NOG peptide N54 and its c-peptide CN54; NOG peptide N77 and its c-peptide CN77; SOST peptide S146). Compared to individuals with mechanical back pain, AS patients have significantly higher levels of IgGs which bind to all 5 peptides: NOG c-peptide CN54 (p=0.003; FIG. 13a), NOG peptide N54 (p<0.001; FIG. 4a), NOG c-peptide CN76 (p=0.003; FIG. 13b), NOG peptide N77 (p<0.001; FIG. 4b) and SOST peptide S146 (p<0.001; FIG. 14).

This study originated from our unexpected observation that treatment of ank/ank mice with NOG led to acceleration of ankylosis progression (data not provided) and concurrent generation of NOG and SOST IgG ICs. This led to our finding that in human sera, autoabs to NOG and SOST are present in healthy individuals but exist at significantly higher levels in sera from AS patients. This represents the first identification of natural autoabs to BMP and Wnt/β-catenin signaling antagonists in humans.

The following comments are made without being bound by any theory.

It is possible that these natural autoabs serve as a feedback mechanism to neutralize the antagonist function of NOG and SOST, and to maintain homeostasis in bone formation during bone remodeling in adult life. As free NOG and SOST are in excess in human sera, it is possible that NOG and SOST IgGs/ICs function locally in joint tissues. Serum SOST levels have been observed to be lower in AS patients[17]. One study reported that SOST expression is absent in osteocytes from AS patients[17]. In view of our novel finding of NOG and SOST IgG ICs, this result needs to be re-interpreted. Autoabs would mask SOST in AS osteocytes, rendering it undetectable. To date, NOG expression in AS patients has not been studied. In relation to immune cells, NOG protein expression was detected in peripheral blood CD3+ T cells and lower levels were found in monocytes[18]. TNF-α upregulates NOG expression in normal peripheral blood lymphocytes in vitro[18].

Autoabs to SOST could arise from different mechanistic pathways such as molecular mimicry or idiotypic(id)/anti-idiotypic network. The fact that autoabs directed to sites where NOG and SOST interact would argue for the later scenario. This possibility is also supported by the fact that when ank/ank mice were treated with NOG, concurrent increased levels of both NOG and SOST IgG ICs were observed (FIG. 15).

Aside from the NOG/SOST epitopes we identified, we expect that there are other yet-to-be identified epitopes. We cannot rule out the possibility that NOG N54 and N77 are in fact 2 components of the same conformational dependent epitope (FIG. 8). There is precedent from other autoab-autoAg systems that immunodominant epitopes are present. Epitope spreading may be observed in situations where the sera were taken from AS patients with long disease duration. Sera from AS patients with early disease prior to treatments would be the most informative for identification of initiating epitopes.

Our identification of enterobacterial antigen-associated NOG and SOST epitopes suggests that these are candidate epitopes that could initiate autoimmunity in AS patients. In vitro and in vivo functionality tests are ongoing.

There is an ongoing debate regarding whether inflammation and ankylosis in AS are linked events or independent processes[10, 11]. For clinicians, this critical issue affects the management strategy for SpA. For example, early intervention with anti-TNF therapy would delay ankylosis development only if inflammation and ankylosis are linked processes. Our results suggest that ankylosis may be triggered by autoimmune responses initiated by enterobacteria antigens, and thus NOG- and SOST-IgG ICs might provide the missing link for the two related processes of inflammation and ankylosis. It is possible that levels of NOG- and SOST-IgG ICs could serve as good biomarkers for monitoring treatment effects as well.

Low back pain, with the life time prevalence of about 70%[19] in the population, is the second most common reason for primary care physician (PCP) consultation after the common cold. 2-4% of these cases will progress to chronic back pain. Over the past decade, the number of individuals in North America experiencing chronic back pain is increasing. It is the number one reason for sick leaves and for work-related disability claims. The current chronic back pain diagnosis recommendation for PCP involves a complicated algorithm which is difficult to comprehend. In many cases, patients with chronic back pain are misdiagnosed even with currently available diagnostic modalities. Mechanical and inflammatory back pain requires different medical treatments, but it remains a recurring challenge to distinguish the two conditions. We have demonstrated that ELISAs for antigen-free IgG binding to 3 peptides (NOG peptide N54, NOG peptide N76 and SOST peptide S146) effectively distinguish individuals with inflammatory versus mechanical back pain. These simple tests could be used as the first-line diagnostics to streamline accurate/efficient diagnosis and to minimize costly diagnostic procedures. Recognizing that there remains an unacceptably long time (5-10 years) for AS diagnosis, the availability of a serological test that would allow earlier diagnosis and treatment would be extremely appealing in terms of health care improvement and cost reduction.

Although preferred embodiments of the invention have been described herein, it will be understood by those skilled in the art that variations may be made thereto without departing from the spirit of the invention or the scope of the appended claims. All documents disclosed herein are incorporated by reference.

REFERENCE LIST 1. van der Linden S, Valkenburg H, Cats A. Evaluation of diagnostic criteria for ankylosing spondylitis. A proposal for modification of the New York criteria. Arthritis Rheum 1984; 27:361-8.
2. Reveille J D, Witter J P, Weisman M H. Prevalence of axial spondylarthritis in the United States: estimates from a cross-sectional survey. Arthritis Care Res (Hoboken) 2012; 64:905-10.
3. Feldtkeller E, Khan M A, van der Heijde D, et al. Age at disease onset and diagnosis delay in HLA-B27 negative vs positive patients with ankylosing spondylitis. Rheumatol Int 2003; 23:61-6.
4. Rudwaleit M, van der Heijde D, Khan M A et al. How to diagnosis axial spondyloarthritis early. Ann Rheum Dis 2004; 63:535-43.
5. van der Heijde D, Landewé R, Einstein S et al. Radiographic progression of ankylosing spondylitis after up to two years of treatment with etanercept. Arthritis Rheum 2008; 58:1324-31.
6. Jacques P, Elewaut D, Mielants H. Interaction between gut inflammation and arthritis/spondylitis. Curr Opin Rheumatol 2010; 22:368-74.
7. Sieper J. Pathogenesis of reactive arthritis. Curr Rheumatol Rep 2001; 3:412-8.
8. Leirisalo-Repo M, Mattila L. Microbial factors in spondyloarthropathies: insights from population studies. Curr Opin Rheumatol 2003; 15:408-12.
9. Zambrano-Zaragoza J F, Duran-Avelar M J, Rodriguez-Ocampo A N et al. The 30-Kd band from *Salmonella typhimurium*: IgM, IgA and IgG antibody response in patients with ankylosing spondylitis. Rheumatol. 2009; 48:748-54.
10. Lories R J U, Dougados M. Inflammation and ankylosis: still an enigmatic relationship in spondyloarthritis. Ann Rheum Dis 2012; 71:317-8.
11. Maksymowych W P, Elewaut D, Schett G. Motion for debate: the development of ankylosis in ankylosing spondylitis is largely dependent on inflammation. Arthritis Rheum 2012; 64:1713-9.
12. Ho A M, Johnson M D, Kingley D M. Role of the mouse ank gene in control of tissue calcification and arthritis. Science 2000; 289:265-70.
13. Las Heras F, Pritzker K P H, So A et al. Aberrant chondrocyte hypertrophy and activation of β-catenin signaling precede joint ankylosis in ank/ank mice. J Rheumatol 2012; 39:583-93.
14. Wright C, Sibani S, Trudgian D et al. Detection of multiple autoantibodies in patients with ankylosing spondylitis using nucleic acid programmable protein arrays. Mol Cell Proteomics 2012; 11:M9.00384.
15. Lories R J, Derese I, Luyten F P. Modulation of bone morphogenetic protein signaling inhibits the onset and progression of ankylosing enthesitis. J Clin Invest 2005; 115:1571-9.
16. Winkler D G, Yu C, Geoghegan J C et al. Noggin and Sclerostin bone morphogenetic protein antagonists form a mutually inhibitory complex. J Biol Chem 2004; 279:36293-8.
17. Appel H, Ruiz-Heiland G, Listing J et al. Altered skeletal expression of sclerostin and its link to radiographic progression in ankylosing spondylitis. Arthritis Rheum 2009; 60:3257-62.
18. Urshansky N, Mausner-Fainberg K, Auriel E et al. Reduced production of noggin by immune cells of patients with relapsing-remitting multiple sclerosis. J Neuroimmunol 2011; 232:171-8.
19. Freburger J K, Holmes G M, Agans R P et al. The rising prevalence of chronic low back pain. Arch Intern Med 2009; 169:251-8.

The invention claimed is:

1. A method for diagnosing a subject with Ankylosing Spondylitis comprising: a. providing a sample from the subject suspected having Ankylosing Spondylitis; b. detecting a level of autoantibodies to at least one of Noggin (NOG) and Sclerostin (SOST) in the sample; c. comparing the level of autoantibodies detected in b. to a level of autoantibodies in a control sample; wherein a relatively higher level of autoantibodies in the subject sample compared to the control sample is indicative of Ankylosing Spondylitis in the subject.

2. A method for prognosticating Ankylosing Spondylitis in a subject comprising: a. providing a sample from the subject; b. detecting a level of autoantibodies to at least one of NOG and SOST in the sample; c. comparing the level of autoantibodies detected in b. to a level of autoantibodies in a control sample; wherein a relatively higher level of autoantibodies in the subject sample compared to the control sample is at least one of (i) indicative of the likelihood of the subject to have progression in ankylosis and (ii) a predictor of severity of disease.

3. The method of claim 1, wherein the level of autoantibodies in the sample compared to the control sample is 2-10.times. higher.

4. The method of claim 1, wherein samples are one of serum, plasma and synovial fluid samples.

5. The method of claim 1, wherein the autoantibodies are pre-complexed with antigen.

6. The method of claim 5, wherein the autoantibody is in a NOG-IgG immune complex.

7. The method of claim 5, wherein the autoantibody is in a SOST-IgG immune complex.

8. The method of claim 5, wherein the autoantibody is in a NOG/SOST-IgG immune complex.

9. The method of claim 1, wherein the level of autoantibodies to at least one of NOG and SOST in the sample is detected using at least one peptide capable of selectively binding to autoantibodies to at least one of NOG and SOST.

10. The method of claim 9, wherein the peptide comprises conserved residues, the conserved residues being one of: a. residues 5-18 of N54 (SEQ ID NO. 1); b. residues 3, 4, 6, 8, 9, 11, 12, 13, 15 and 16 of CN54 (SEQ ID NO. 2); c. residues 6-13 of N77 (SEQ ID NO. 3); d. residues 7-14 CN76 (SEQ ID NO. 4); and e. residues 3-7 and 9-12 of S146 (SEQ ID NO. 5).

11. The method of claim 10, wherein the conserved residues are one of: a. residues 5-18 of N54 (SEQ ID NO. 1); b. residues 3, 4, 6, 8, 9, 11, 12, 13, 15 and 16 of CN54 (SEQ ID NO. 2); c. residues 6-13 of N77 (SEQ ID NO. 3); d. residues 7-14 CN76 (SEQ ID NO. 4); and e. residues 3-7 and 9-12 of S146 (SEQ ID NO. 5).

12. The method of claim 9, wherein the peptide is 6-30 amino acids in length.

13. The method of claim 9, wherein the peptide is at least one of N54, CN54, N77, CN76 and S146.

14. The method of claim 10, wherein the peptide of b. comprises residues 3-16 of SEQ ID NO:2.

15. The method of claim 10, wherein the peptide of e. comprises residues 3-12 of SEQ ID NO:5.

* * * * *

UNITED STATES PATENT AND TRADEMARK OFFICE
CERTIFICATE OF CORRECTION

PATENT NO. : 8,895,254 B2  Page 1 of 1
APPLICATION NO. : 14/233342
DATED : November 25, 2014
INVENTOR(S) : Florence Wing Ling Tsui et al.

It is certified that error appears in the above-identified patent and that said Letters Patent is hereby corrected as shown below:

In the Claims

In Claim 3 on column 13, line 58, "2-10.times." should read --2-10 times--.

In Claim 11 on column 14, line 55, "5146" should read --S146--.

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,895,254 B2  
APPLICATION NO. : 14/233342  
DATED : November 25, 2014  
INVENTOR(S) : Florence Wing Ling Tsui et al.

Page 1 of 1

It is certified that error appears in the above-identified patent and that said Letters Patent is hereby corrected as shown below:

In the Drawings

On drawing Sheet 10 in Fig. 9b the label "NOG c-peptide (CN76):" should read --NOG c-peptide (CN77):--.

On drawing Sheet 15 in Fig. 13b the label "NOG c-peptide (CN76):" should read --NOG c-peptide (CN77):--.

In the Specification

In Column 2 on line 26 delete "CN76" and insert --CN77-- therefor.

In Column 5 on line 20 delete "CN76" and insert --CN77-- therefor.

In Column 5 on line 27 delete "CN76" and insert --CN77-- therefor.

In Column 9 on line 56 delete "CN76" and insert --CN77-- therefor.

In the Claims

In Column 14 on line 48 (Claim 10) delete "CN76" and insert --CN77-- therefor.

In Column 14 on line 54 (Claim 11) delete "CN76" and insert --CN77-- therefor.

In Column 14 on line 59 (Claim 13) delete "CN76" and insert --CN77-- therefor.

Signed and Sealed this  
Twenty-second Day of September, 2015

Michelle K. Lee  
*Director of the United States Patent and Trademark Office*